United States Patent [19]

Jaeger

[11] Patent Number: 5,637,808
[45] Date of Patent: Jun. 10, 1997

[54] LIQUID PRODUCT SAMPLER

[76] Inventor: Ben E. Jaeger, 50 Hunter La., Yorkville, Ill. 60560

[21] Appl. No.: 564,850

[22] Filed: Nov. 30, 1995

[51] Int. Cl.⁶ .................................................... G01N 1/20
[52] U.S. Cl. ............................................... 73/863.83
[58] Field of Search ..................... 73/863.52, 863.54, 73/863.86, 863.83, 863.82, 863.71–863.73, 864.31, 864.32, 863.84

[56] References Cited

U.S. PATENT DOCUMENTS

| | | |
|---|---|---|
| 3,587,324 | 6/1971 | Bandy, Jr. . |
| 3,751,992 | 8/1973 | Morgan ................. 73/863.83 |
| 4,018,418 | 4/1977 | Dion-Biro . |
| 4,147,062 | 4/1979 | Jaeger . |
| 4,262,533 | 4/1981 | Jaeger . |
| 4,475,410 | 10/1984 | Jaeger . |
| 4,487,080 | 12/1984 | Leaseburg et al. ................. 73/863.83 |
| 4,562,749 | 1/1986 | Clark . |
| 4,625,571 | 12/1986 | Slater . |
| 4,635,470 | 1/1987 | Skallen et al. ................. 73/863.83 |
| 4,744,255 | 5/1988 | Jaeger . |
| 4,810,392 | 3/1989 | Fulton et al. . |
| 4,903,765 | 2/1990 | Zunkel . |
| 5,176,035 | 1/1993 | Hartstone . |

*Primary Examiner*—Robert Raevis
*Attorney, Agent, or Firm*—Juettner Pyle Lloyd & Piontek

[57] ABSTRACT

A sampling apparatus is characterized by a housing having a liquid product flow passage and an outlet port extending between the passage and the housing exterior. A plunger having a recess toward its nose extends across the passage and the nose of the plunger is received in the outlet port. The plunger is reciprocable between a first position where the recess is in communication with the passage to receive in the recess a sample of liquid product and a second position where the recess is moved out of the passage and through the outlet port into communication with a sample collection point to the exterior of the housing to deliver the product sample to the collection point. A seal is always maintained through the outlet port between the passage and the housing exterior, and a sample collection bottle is releasably carried by the housing at the collection point.

18 Claims, 2 Drawing Sheets

LIQUID PRODUCT SAMPLER

BACKGROUND OF THE INVENTION

The present invention relates to sampling apparatus, and in particular to a sampling apparatus for extracting a sample of liquid product from a product flow line and for delivering the sample in a sanitary condition to a collection container.

Modern process control often requires that the immediate or overall composition of a liquid product flowing through a pipe or conduit be monitored. Such monitoring can be accomplished with apparatus that takes samples of the liquid from the main body thereof. Where a composite sample of the liquid flow is required, the sampler is usually operated to withdraw a series of small, precisely measured discrete amounts of the liquid as it passes the sampling point. The number of individual samples taken is adjusted according to time or by liquid product volume flow to generate a composite sample volume that represents the process material composition. Samples can be collected in a common container or in individual bottles as required.

Samplers are used to obtain samples of milk for analysis. Milk is received by a dairy from a number of individual dairy farmers and tank trucks transport the milk from the dairy farmers to the dairy. A single tank truck may receive milk from as many as ten different dairy farmers before delivering the load of milk to the dairy. Because the batches of milk supplied by the individual dairy farmers ordinarily differ in content, such as in percentage of butterfat, it is necessary to know the amount and content of the milk supplied by each dairy farmer in order to determine the payment due to the farmer.

A milk storage tank at each dairy farm has an agitator and a cooler to keep the milk thoroughly stirred and in a chilled condition, and at each dairy farm the operator of the tank truck "examines" the milk in the storage tank to determine whether to load it into the truck. The decision to load or not load the milk is based upon various tests such as smelling the milk, determining that it is properly agitated, and measuring the temperature of the milk to ensure that there will not be rapid spoilage.

If the truck operator determines that the milk in the storage tank seems to be satisfactory, it is loaded into the tank truck where it mixes with milk from other dairy farms. Prior to or during loading, the amount of milk supplied by the dairy farmer is determined and a sample of the milk is obtained for later analysis to determine its content. To obtain a sample the truck operator could hand dip a sample of milk from the dairy farm storage tank, but the procedure is expensive and time consuming and is prone to operator error. Instead, as the milk is flowed from the storage tank into the truck, the better practice is to periodically extract and collect discrete and measured amounts of milk from the flow to obtain a composite sample for analysis.

The operator of the tank truck obtains a sample of milk from each dairy farmer and each sample is analyzed at the dairy for such things as butterfat and calcium content, as well as for any undesirable substances such as bacteria, steroids, insecticides and other objectionable contaminants. The samples representing the various batches of milk in the truck may be analyzed before the truck is unloaded at the dairy. This enables a determination to be made as to whether a truck load of milk obtained from a group of dairy farmers is unacceptable before the milk in the truck is unloaded and mixed with other milk at the dairy.

In sampling milk, it is necessary to maintain the highest possible level of sanitation in order to avoid problems with bacterial build-up and contamination. Because sampling often occurs at the tank truck as a batch of milk from a dairy farmer's holding tank is flowed into the truck, the same sampler is used in sampling the different batches of milk flowed into the truck at the various dairy farms. The sampler should therefore be capable of being thoroughly cleaned and brought to a sanitary condition between uses to prevent cross-contamination of samples of milk as a result of bacteria or other contaminants being conveyed or carried over by the sampler from milk at one dairy farm to milk at the next.

OBJECTS OF THE INVENTION

An object of the invention is to provide a sampler which can withdraw small measured samples of a liquid product from a product line.

Another object is to provide such a sampler which can readily be thoroughly cleaned in place after sampling one batch of product and before sampling another to maintain the integrity of the samples.

A further object is to provide such a sampler in which a sample of product is transported directly from a product line to a collection container without first passing through dead space in the sampler.

A still further object is to provide such a sampler that is of simple and economical construction and may readily and conveniently be disassembled for cleaning.

Yet another object is to provide such a sampler in which there is a significantly decreased carryover of product from one sample to the next.

SUMMARY OF THE INVENTION

In accordance with the present invention, a sampling apparatus has body means having passage means for liquid product, outlet port means extending between the passage means and the exterior of the body means, and bore means opening to the passage means opposite from the outlet port means. Also included is plunger means that has a nose at its forward end, a recess rearwardly from the nose and an elongate member rearwardly from the recess. The plunger means is carried by the body means with its elongate member slidably received in the bore means and extending forwardly from the bore means opening across the passage means, and with the recess and nose slidable in the outlet port means. Means are provided for reciprocating the plunger means to retract the recess through the outlet port means into communication with the passage means to receive a sample of liquid product in the recess, and to then extend the recess with the product sample therein through the outlet port means into communication with a sample collection point to the exterior of the body means for discharge of the product sample from the recess to the collection point. To prevent a free flow of product from the passage means, seal means maintains a seal through the outlet port means.

To facilitate release of the liquid product sample from the plunger means recess, the surfaces of the recess and nose are advantageously of a nonwetting material and, additionally, the sampling apparatus is oriented so that a longitudinal axis of the plunger means is tilted with respect to vertical to promote outflow of the product sample from the recess. The recess may comprise an annular recess, and the seal means for maintaining a seal through the outlet port means includes first and second seal means on the plunger means on opposite sides of the recess, the arrangement being such that upon reciprocation of the plunger means, at least one of the first and second seal means always remains in and seals the plunger means to the outlet port means. The passage means extends through the body means, and included are means for coupling the body means in a product line with the passage means in series with the product line.

The foregoing and other objects, advantages and features of the invention will become apparent upon a consideration of the following detailed description, when taken in conjunction with the accompanying drawings.

DETAILED DESCRIPTION

The Prior Art

Figure 1:
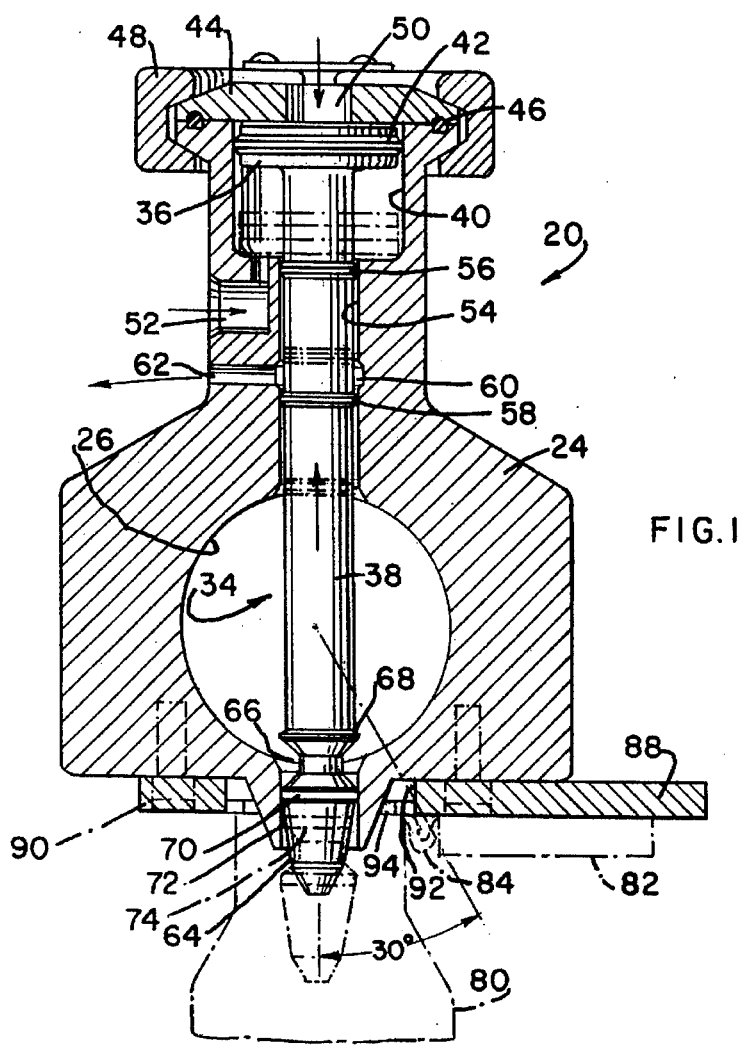
FIG. 1 is a cross sectional front elevation view of a liquid product sampler constructed according to a preferred embodiment of the invention.

To better appreciate the advantages and features of the present invention, a prior art sampler of the plunger type, as taught by U.S. Pat. No. 4,147,062, will first be considered. Such prior sampler is characterized by a housing having a bore. The housing is supported with one end of the bore communicating with the interior of a liquid containing vessel, and a plunger having an annular recess is in the bore. The plunger is reciprocated in the bore to project the recess into the vessel to receive a sample of liquid therein, and to then retract the recess and sample therein from the vessel to an intermediate sample receiving chamber in the bore for discharge of the liquid sample through a housing outlet to a sample collection point. Seals on the plunger on opposite sides of the recess maintain a liquid seal through the bore between the vessel and the sample receiving chamber to prevent a free flow of liquid from the vessel to the chamber. The sample receiving recess is of a size to contain a precisely measured amount of liquid product, and the sampler may be cyclically actuated so that the samples collected represent a true composite sample of the liquid in the vessel.

While said U.S. Pat. No. 4,147,062 teaches use of the sampler to obtain discrete samples of product from a vessel, the sampler could just as readily be operated in a reverse manner. In other words, it could be used to deliver discrete amounts of liquid product from the inner sample receiving chamber in the bore of the housing to the interior of the vessel. When used in such manner the sampler would operate as a pump, since it would then effectively transfer liquid from the sample receiving chamber into the vessel.

While the sampler of said U.S. Pat. No. 4,147,062 can be operated as a pump, when operated in the manner taught by said patent the annular sample receiving recess in the plunger is washed by liquid product each time it is extended into the vessel, and movement of a liquid sample from the vessel to the sample receiving container is accomplished such that the samples collected are true samples of the liquid in the vessel. However, should the sampler be used to sample different batches of liquid product, it would be possible for product residue from one batch to remain in a dead space in the sampler and be carried over to and contaminate a sample obtained from the next batch of product. For example, if the sampler were used to sample a batch of milk from one dairy farmer, milk residue from the batch could potentially remain in a dead space in the sampler even after cleaning of the sampler in place upon completion of sampling the batch, and thereby be carried over by the sampler and introduced into a sample obtained from the next batch.

For a more detailed description of this conventional sampler, reference is made to U.S. Pat. No. 4,147,062, issued to the present inventor on Apr. 3, 1979, the entirety of the teachings of which are specifically incorporated herein by reference.

The Invention

Referring to the drawings, there is indicated generally at 20 a sampler according to a preferred embodiment of the invention. The sampler is uniquely structured to overcome the aforementioned disadvantages of prior samplers, and is for connection in a product line 22 through which liquid product flows, such that a passage through the sampler is in series with the product line for flow of liquid product through the sampler passage. The sampler has a plunger assembly that extends diagonally across the passage for receiving within an annular recess in the plunger a sample of the product, and a forward nose of the plunger is reciprocable through an outlet port from the passage to move the recess and sample therein to a collection point to the exterior of the sampler. The sampler may be cyclically operated so that collected product samples represent a composite sample of product flowing through the line, and seals on the plunger assembly maintain a liquid seal through the outlet port between the sampler passage and the collection point to the exterior of the sampler. The annular recess is washed clean by the product flow each time a sample is obtained from the product line, so the collected samples accurately represent the product in the line.

More specifically, the sampler 20 comprises a housing or body 24 through which a product flow passage 26 extends. The sampler is adapted to be removably connected in series with the product line 22, and for the purpose the body has annular flanges 28 at opposite ends of and around the passage 26. Facing ends of the product line 22, between which the sampler is connected, have annular flanges 30, whereby the sampler may conveniently be connected in the product line by a pair of quick release clamps 32, with the sampler passage 26 in series with the product line.

The sampler 20 has a plunger assembly, indicated generally at 34, mounted for reciprocation in the body 24. Motor means for reciprocating the plunger assembly includes a piston 36 at an upper or rearward end of a cylindrical body 38 of the plunger assembly. The piston is in a cylinder 40 in an upper end of the body 24 and is sealed to the cylinder by a seal 42. A cap 44 is sealed to the upper end of the body across the cylinder by a seal 46, and is connected to the body by a quick release clamp 48 that extends around mating annular flanges on the cap and body, whereby the cap may readily be detached from the body for convenient removal of the entirety of the plunger assembly should it be necessary to do so to clean the sampler. An air inlet 50 in the cap communicates with the cylinder on an upper side of the piston and an air inlet 52 in the body communicates with the cylinder on a lower side of the piston. Pressurized air at the inlet 50 moves the piston and plunger assembly forwardly or downwardly (as shown in the drawings), while pressurized air at the inlet 52 moves the piston and plunger assembly rearwardly or upwardly.

Figure 1A:
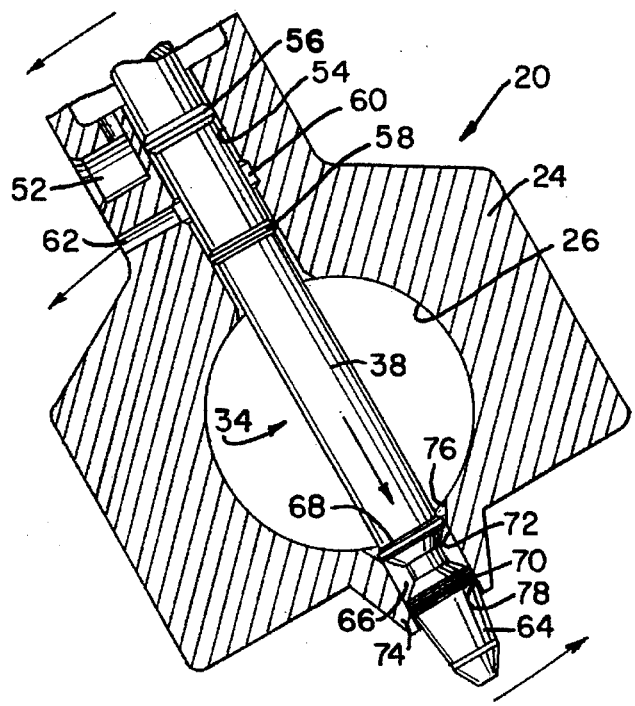
FIG. 1a is a fragmentary cross sectional front elevation view of the sampler, showing the sampler tilted with respect to vertical to facilitate release of product samples from the sampler.
Figure 2:
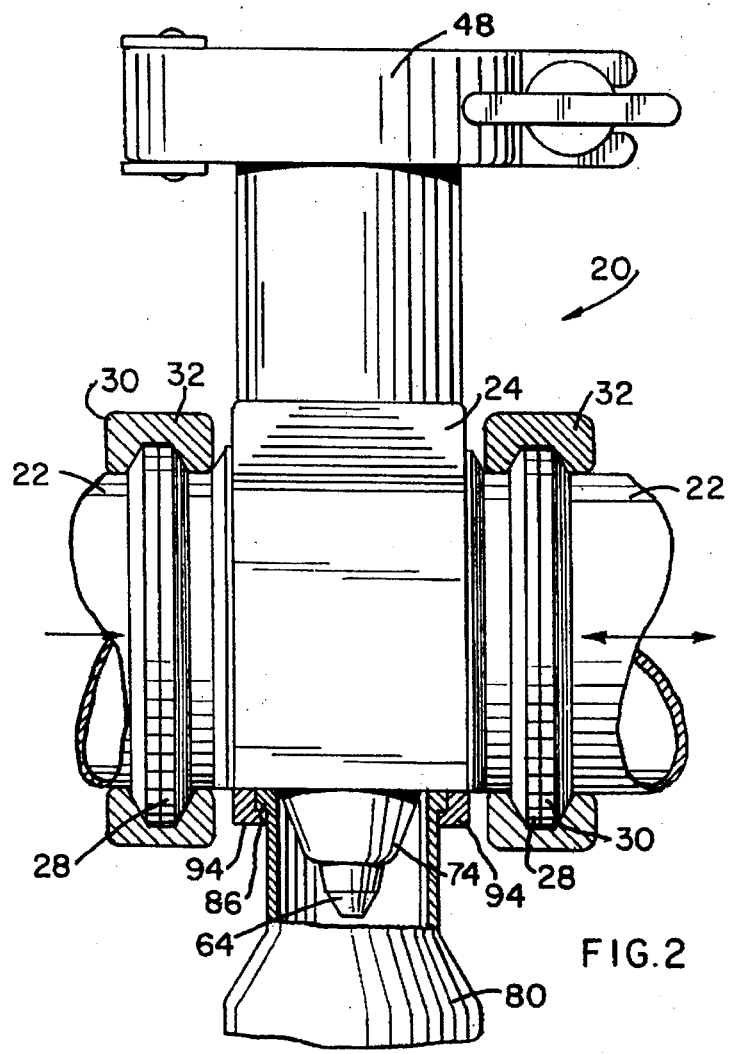
FIG. 2 is a side elevation view of the sampler, showing the sampler connected in a product line from which samples of liquid product are obtained.
Figure 3:
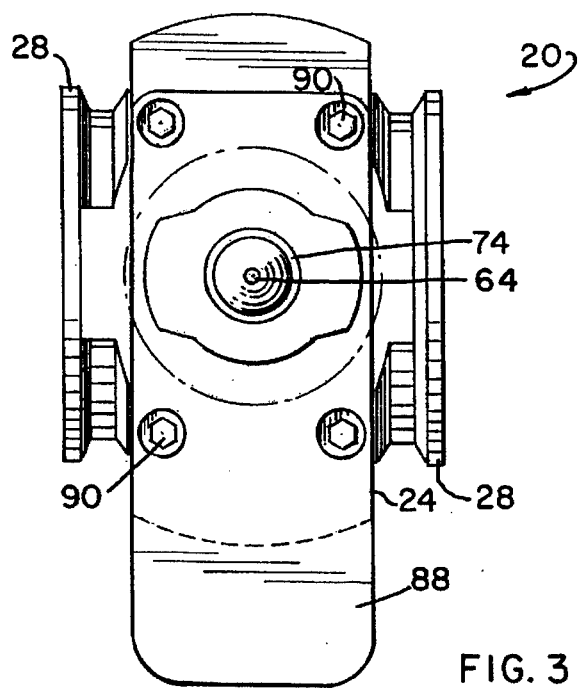
FIG. 3 is a bottom plan view of the sampler.

From the piston 36 the cylindrical body 38 of the plunger assembly 34 extends forwardly through a bore 54 in the body 24 into and through the product flow passage 26. The plunger assembly is sealed with the bore by a pair of seals 56 and 58, an annular recess 60 in the body 24 opens into the bore, and a vent 62 in the body extends between the annular recess and the exterior of the body. The extent of reciprocation of the plunger assembly is defined by the lengths of the cylinder 40 and piston 36, and together with the spacing between the seals 56 and 58 is such that the seal 56 always remains in the bore 54 between the cylinder and the annular recess, while the seal 58 always remains in the bore between the annular recess and an outlet from the bore at the product flow passage 26, to prevent liquid product from flowing through the bore. Should some liquid product seep past the seal 58, it will enter the annular recess and flow out of the sampler through the vent, which outward flow is facilitated by the sampler advantageously being used in a tilted position (FIG. 1a).

From the bore 54 the plunger assembly cylindrical body 38 extends diagonally across the product flow passage 26 to a forward end or nose 64 of the plunger assembly. Behind or rearwardly of the nose the cylindrical body has a liquid product sample receiving recess 66 that may take the form of an annular sample chamber of predetermined volumetric capacity. Seals 68 and 70 are on the plunger assembly on opposite sides of the sample chamber and, along with the seal 58, comprise seal material that is bonded to the plunger assembly and ground to the desired shape. These seals contact the liquid product, and by virtue of being bonded to the plunger assembly, they present no openings into which liquid product can enter and possibly remain. Consequently, they do not provide an opportunity for product residue to become trapped and cause an unsanitary condition in the sampler, and possibly be carried over from one sample to the next, which is particularly important when a food product such as milk is sampled.

The forward end of the plunger assembly 34 extends into an outlet port 72 in a frustoconical extension 74 of the sampler body 24. The outlet port extends between the product flow passage 26 and a sample collection point to the exterior of the sampler, and has a length greater than the distance between the plunger assembly seals 68 and 70. The arrangement is such that upon introduction of air at the inlet 52 so that the plunger assembly fully rearwardly retracted, as shown in solid lines in FIG. 1, the seal 68 and the sample chamber 66 are placed into communication with the product flow passage 26, while the seal 70 is in and seals the plunger assembly to the outlet port to maintain a seal between the product flow passage 26 and the exterior of the sampler. Then, upon introduction of air at the inlet 50 to extend the plunger assembly forwardly, as seen in FIG. 1a the seal 68 enters the outlet port 72 before the seal 70 exits the outlet port, at which time a sample of product received in the sample chamber 66 is captured in the sample chamber while a seal continues to be maintained through the outlet port. Upon full forward extension of the plunger assembly, as shown in phantom lines in FIG. 1, the seal 70 and the sample chamber are moved out of the outlet port and to the exterior of the sampler body and into communication with a sample collection point for release of the product sample from the sample chamber for collection, while the seal 68 remains in and seals the plunger assembly to the outlet port to continue to maintain a seal through the outlet port between the product flow passage and the exterior of the sampler. To facilitate movement of the seals 68 and 70 into the outlet port upon reciprocation of the plunger assembly, chamfers 76 and 78 are at opposite ends of the outlet port. Thus, by virtue of the plunger assembly seals 68 and 70 on opposite sides of the sample chamber 66, product samples may be delivered from the product flow passage to a collection point to the exterior of the sampler while at all times a seal is maintained in the outlet port so that product in the product flow passage cannot freely flow through the outlet port.

Means for receiving and collecting samples of product at the collection point comprises a deformable plastic bottle or vial 80 having a cap 82 connected to its neck by a web 84, all of the bottle, cap and web advantageously being an integral, one-piece plastic material structure. As is conventional, the bottle has a radially outwardly extending circumferential lip 86 around its upper opening, which lip enters an inner circular recess (not shown) in the cap when the cap closes the bottle to releasably retain the cap on the bottle. The lip also is advantageously used to releasably attach the bottle to and retain the bottle on a bottle adaptor plate 88 mounted on a lower end of the sampler body 24 by a plurality of fasteners 90. The frustoconical body extension 74 extends through an opening 92 in the adaptor plate and a pair of downwardly depending diametrically opposed L-shaped semicircular flanges 94 are on the adaptor plate on opposite sides of the opening. To releasably attach the bottle to the adaptor plate around the outlet port 72, the cap 82 is removed from the top of the bottle and held outwardly away from the bottle and the upper end of the bottle is squeezed to an oval configuration and then positioned between the L-shaped flanges and allowed to expand, so that the lip 86 at the top of the bottle moves into the L-shaped flanges. This releasably attaches the bottle to the adaptor plate with the cap abutting the underside of the adaptor plate. With the bottle so supported by the sampler 20, product samples delivered to the collection point to the exterior of the sampler will be discharged from the sample chamber 66 into the bottle.

Due to the small overall volume of each product sample in the plunger assembly recess 66 and surface tension, substantially all of the sample of liquid product may not always readily flow out of the sample chamber and off of the forward end of the plunger assembly 34 at the collection point. Consequently, to promote release of the product sample from the sample chamber and the forward end of the plunger assembly, the surfaces of the sample chamber and of the nose 64 are advantageously made of nonwetting material. To further promote release of the product sample, it is advantageous that the sampler not be mounted vertically, but instead that it be tilted at an angle with respect to vertical, i.e., such that the longitudinal axis of the plunger assembly is inclined with respect to vertical. Tilting the sampler at an angle of more than 20°, and preferably at an angle of about 30° or more with respect to vertical, has been found to yield beneficial results. Tilting the sampler so that the vent 62 extends downwardly provides the additional benefit of positive drainage out of the vent should the seal 58 leak, and tilting also positions the outlet port 72 and the bottle adaptor plate 88 in a more visible and accessible position to facilitate placement and replacement of sample collection bottles 80.

It may be appreciated that the sampler 20 provides increased sanitation in obtaining liquid product samples. Unlike conventional plunger-type samplers in which a product sample extracted from a product line is often conveyed through a dead space in the sampler before being delivered to a collection point, the sampler 20 is structured such that the product sample passes substantially directly from the product line to the collection point. The unique structure of the sampler eliminates any dead areas through which the product sample must be conveyed, and thereby significantly decreases the potential for product residue to collect in the sampler and contaminate either subsequent batches of product or subsequent samples. Also, because the product contacting seals on the plunger assembly are bonded to the plunger assembly and ground to shape, they do not present any openings or crevices in which product residue can collect. Further, the structure of the sampler enables it to easily be disassembled for convenient and thorough cleaning, simply by removing the cap 44 to gain access to the plunger assembly 34 for removal from the body 24.

While the sampler 20 can be disassembled for cleaning, its unique structure normally enables it to be thoroughly and conveniently cleaned in place with a cleaning solution. One reason it can be thoroughly cleaned while in place is because its structure does not accommodate an accumulation of product residue within the sampler. This is because upon each retraction of the plunger assembly 34, its seal 68 and sample collecting recess 66 are washed by product in the passage 26. Then, upon each extension of the plunger assembly, its seal 58 is washed by product in the product passage, while product flowing out of its recess at the collection point flows across and washes the plunger assembly seal 70 and nose 64. The structure of the sampler is therefore such as to inhibit any significant collection of product residue within the sampler, with the result that the sampler can be quite thoroughly cleaned while in place and without need for disassembly.

To clean the sampler 20 in place, cleaning solution can be substituted for product in the line 22, or the sampler can be disconnected from the product line and connected to a supply of cleaning solution. With cleaning solution in the sample passage 26, the sampler is operated through several cycles to "sample" the cleaning solution and thoroughly clean the sampler. To facilitate cleaning it is contemplated that an additional port be in communication with the body recess 60 opposite from the port 62 for flow of cleaning solution through one port into the recess 60 and the space around the plunger assembly between the seals 56 and 58, and then out of the other port.

While the invention has been described in detail, various modifications and other embodiments thereof may be devised by one skilled in the art without departing from the spirit and scope of the invention, as defined in the appended claims.

What is claimed is:

1. A sampling apparatus, comprising:
   housing means having passage means for liquid product and outlet port means extended between said passage means and the exterior of said housing means;
   plunger means having recess means;
   means for reciprocating said plunger means in said outlet port means to retract said recess means rearwardly into communication with said passage means to receive a sample of liquid product therein and to then extend said recess means forwardly through said outlet port means to the exterior of said housing means for discharge of the product sample from said recess means to a sample collection point; and
   means for maintaining a seal through said outlet port means between said passage means and the exterior of said housing means,
   wherein said means for maintaining a seal through said outlet port means includes first and second seal means on said plunger means on opposite sides of said recess means for sealing said plunger means to said outlet port means, said first and second seal means are bonded to said plunger means such that there are substantially no openings between said first and second seal means and said plunger means into which liquid product can enter, said outlet port means has a length that is greater than the distance between said first and second seal means along a longitudinal axis of said plunger means, and said reciprocating means reciprocates said plunger means such that at least one of said first and second seal means always remains in and seals said plunger means to said outlet port means.

2. A sampling apparatus as in claim 1, further comprising:
   container means to the exterior of and supportable by said housing means for receiving and collecting product samples discharged from said plunger means recess means.

3. A sampling apparatus as in claim 1, wherein said recess means comprises an annular recess in said plunger means.

4. A sampling apparatus as in claim 1, wherein said plunger means includes an elongate body extending rearwardly from said recess means and across said passage means, and a nose extending forwardly from said recess means, said nose being moved through said outlet port means to the exterior of said housing means when said recess means is extended forwardly to the exterior of said housing means.

5. A sampling apparatus as in claim 4, wherein said housing means has a bore that opens to said passage means and is coaxial with said outlet port means, said plunger means elongate body extends rearwardly from said recess means across said passage means and into said bore and is slidable in said bore, and said means for reciprocating includes motor means coupled to said elongate body for reciprocating said plunger means.

6. A sampling apparatus as in claim 4, wherein surfaces of said recess means and said nose comprise a nonwetting material to facilitate flow of a sample of liquid product out of said recess means and off of said nose.

7. A sampling apparatus as in claim 1, wherein said passage means extends through said housing means, and said housing means has coupling means at opposite ends of said passage means for connecting said housing means in a liquid product line with said passage means in series with the liquid product line for flow of liquid product through said passage means.

8. A sampling apparatus, comprising:
   body means having passage means for liquid product, outlet port means extending between said passage means and the exterior of said body means, and bore means extending coaxial to said outlet port means and opening to said passage means;
   plunger means having a nose at its forward end, a recess rearwardly from said nose, and an elongate member extending rearwardly from said recess, said plunger means being carried by said body means with said elongate member slidably received in said bore means and extending forwardly through said bore means opening and across said passage means to said recess and with said recess and said nose being slidable in said outlet port means;
   means for reciprocating said plunger means to retract said recess rearwardly into communication with said passage means to receive a sample of liquid product in said recess and to then extend said recess and product sample therein forwardly through said outlet port means to the exterior of said body means for discharge of the product sample from said recess to a sample collection point; and means for maintaining a seal through said outlet port means between said passage means and the exterior of said body means, wherein said seal maintaining means includes first and second seal means on said plunger means on opposite sides of said recess for sealing said plunger means to said outlet port means, said first and second seal means are bonded to said plunger means such that there are substantially no openings between said first and second seal means and said plunger means into which liquid product can enter, said outlet port means has a length that is greater than the spacing between said first and second seal means, and said reciprocating means reciprocates said plunger means such that at least one of said first and second seal means always remains in and seals said plunger means to said outlet port means.

9. A sampling apparatus as in claim 8, wherein surfaces of said plunger means recess and nose are of a nonwetting material to facilitate flow of a sample of liquid product out of said recess means and off of said nose.

10. A sampling apparatus as in claim 8, wherein said plunger means has a longitudinal axis and in operation of said sampling apparatus said plunger means longitudinal axis is inclined at an angle with respect to vertical.

11. A sampling apparatus as in claim 10, wherein in operation of said sampling apparatus said plunger means longitudinal axis is inclined at an angle of at least 30° with respect to vertical.

12. A sampling apparatus as in claim 8, wherein said recess comprises an annular recess in said plunger means between said plunger means nose and elongate member.

13. A sampling apparatus as in claim 8, wherein said passage means extends through said body means, and including means for coupling said body means in a product line with said passage means in series with the product line.

14. A sampling apparatus as in claim 8, wherein said means for reciprocating comprises motor means coupled to said elongate member.

15. A sampling apparatus as in claim 8, further including means for sealing said plunger means elongate member to said bore means, and vent means in said body means between said bore means and the exterior of said body means for venting from said bore means any product that leaks past said means for sealing said plunger means elongate member to said bore means.

16. A sampling apparatus as in claim 8, including a sample collection container to the exterior of and supportable by said body means for receiving and collecting product samples discharged from said recess.

17. A sampling apparatus as in claim 16, wherein said sample collection container has an inlet opening, and including means for releasably supporting said sample collection container with its inlet opening adjacent to an outlet from said outlet port means.

18. A sampling apparatus as in claim 8, wherein said sample collection container is resiliently deformable and has a lip extending outwardly from around said inlet opening thereto, and said means for releasably supporting said sample collection container comprises mounting means on said body means for releasably receiving said lip upon deformation of said collection container and said lip thereof to releasably support said sample collection container on said body with said inlet opening to said sample collection container adjacent to and around said outlet from said outlet port means.

* * * * *